(12) United States Patent
Kim et al.

(10) Patent No.: US 10,724,167 B2
(45) Date of Patent: Jul. 28, 2020

(54) BATHROOM MANAGEMENT APPARATUS

(71) Applicant: LG ELECTRONICS INC., Seoul (KR)

(72) Inventors: Jeongyun Kim, Seoul (KR); Jinhyeon Jeon, Seoul (KR); Daeyun Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 185 days.

(21) Appl. No.: 15/915,253

(22) Filed: Mar. 8, 2018

(65) Prior Publication Data
US 2018/0258579 A1  Sep. 13, 2018

(30) Foreign Application Priority Data

Mar. 8, 2017  (KR) .................. 10-2017-0029724

(51) Int. Cl.
| | | |
|---|---|---|
| *D06F 58/10* | (2006.01) | |
| *A47B 67/00* | (2006.01) | |
| *F25D 11/00* | (2006.01) | |
| *A47B 55/00* | (2006.01) | |

(Continued)

(52) U.S. Cl.
CPC .......... *D06F 58/10* (2013.01); *A47B 47/0091* (2013.01); *A47B 47/042* (2013.01); *A47B 55/00* (2013.01); *A47B 67/005* (2013.01); *A47B 96/04* (2013.01); *A61L 2/26* (2013.01); *F24H 3/022* (2013.01); *F25D 11/00* (2013.01); *A47B 81/00* (2013.01); *A47B 95/008* (2013.01); *A47B 96/20* (2013.01); *A47B 2096/208* (2013.01);

(Continued)

(58) Field of Classification Search
CPC . D06F 58/10; A47B 47/0091; A47B 47/0066; A47B 47/0075; A47B 47/042; A47B 67/005; A47B 81/00
See application file for complete search history.

(56) References Cited

U.S. PATENT DOCUMENTS 5,785,402 A * 7/1998 DeLorenzo ............ A47B 67/04
312/350
6,354,683 B1  3/2002 Benbow
(Continued)

FOREIGN PATENT DOCUMENTS

| CN | 1384913 | 12/2002 |
|---|---|---|
| CN | 201118113 | 9/2008 |
| CN | 204600288 | 9/2015 |

OTHER PUBLICATIONS

Chinese Office Action dated Apr. 10, 2020 issued in CN Application No. 201810189897.5.

*Primary Examiner* — Daniel J Rohrhoff
(74) *Attorney, Agent, or Firm* — Ked & Associates, LLP

(57) ABSTRACT

Disclosed is a firm bath management apparatus. A bathroom management apparatus includes: a cabinet of which a front surface is open; a frame installed at an inner side of the cabinet to reinforce stiffness of the cabinet and of which an upper side and a lower side are spaced apart from the cabinet; an upper cover provided between the cabinet and the upper side of the frame to be coupled with the cabinet and the frame and configured to cover a space between the cabinet and the upper side of the frame; and a control panel provided between the cabinet and the lower side of the frame to be coupled with the cabinet and the frame and installed therein with a user interface.

20 Claims, 16 Drawing Sheets

(51) Int. Cl.
*A47B 47/00* (2006.01)
*A61L 2/26* (2006.01)
*F24H 3/02* (2006.01)
*A47B 47/04* (2006.01)
*A47B 96/04* (2006.01)
*A47B 81/00* (2006.01)
*A61L 2/10* (2006.01)
*A47B 96/20* (2006.01)
*A47B 95/00* (2006.01)
*H02J 7/00* (2006.01)
*A61L 9/20* (2006.01)

(52) U.S. Cl.
CPC . *A61L 2/10* (2013.01); *A61L 9/20* (2013.01); *A61L 2202/11* (2013.01); *H02J 7/0042* (2013.01)

(56) References Cited

U.S. PATENT DOCUMENTS

| | | | |
|---|---|---|---|
| 6,640,581 B1 | 11/2003 | Choi | |
| 8,096,062 B1* | 1/2012 | Bellen | D06F 58/10 |
| | | | 105/202 |
| 10,016,056 B2* | 7/2018 | Sklansky | F16B 12/24 |
| 2001/0017509 A1 | 8/2001 | Hallsten | |
| 2003/0042828 A1* | 3/2003 | Bonin | A47B 67/02 |
| | | | 312/245 |
| 2010/0224615 A1* | 9/2010 | Gallo | A47K 10/06 |
| | | | 219/385 |
| 2013/0118023 A1* | 5/2013 | Cennon | D06F 58/20 |
| | | | 34/202 |
| 2013/0256487 A1 | 10/2013 | Ko | |
| 2013/0327256 A1* | 12/2013 | Glenn, II | A47B 13/00 |
| | | | 108/50.02 |
| 2016/0211689 A1* | 7/2016 | Wang | H02J 7/0045 |
| 2017/0181541 A1* | 6/2017 | Stanley, Jr. | H02J 7/025 |
| 2018/0110382 A1* | 4/2018 | Jeon | A47K 17/00 |
| 2018/0156477 A1* | 6/2018 | Jeon | F24F 13/0272 |
| 2018/0249827 A1* | 9/2018 | Kim | A47B 47/0091 |
| 2018/0249830 A1* | 9/2018 | Jeon | A47B 67/005 |
| 2018/0251932 A1* | 9/2018 | Jeon | A47B 81/00 |
| 2018/0252419 A1* | 9/2018 | Kim | F24F 3/16 |
| 2018/0255923 A1* | 9/2018 | Kim | F25D 11/00 |
| 2018/0259204 A1* | 9/2018 | Jeon | F24F 5/0042 |
| 2018/0299826 A1* | 10/2018 | Nonaka | G03G 21/1857 |

* cited by examiner

BATHROOM MANAGEMENT APPARATUS

CROSS-REFERENCE TO RELATED APPLICATION

This application claims priority under 35 U.S.C. § 119 to Korean Application No. 10-2017-0029724 filed on Mar. 8, 2017, whose entire disclosure is hereby incorporated by reference.

BACKGROUND

1. Field

The present disclosure relates to a bathroom management apparatus and, more particularly, to a bathroom management apparatus which is installed at a wall of a bathroom to store various bath and toilet appliances including towels and to remove humidity in the bathroom.

2. Background

In general, a bathroom is a location where users wash clothes, wash a face, wash hands, shower, or use a toilet. Since the bathroom is generally a humid place, molds and bacteria may easily breed, such that odors may occur in the bathroom.

Most bathrooms dry and deodorize using a ventilation fan. However, an operation of the ventilation fan may not be suitable or may be insufficient to dry the whole bathroom even when the ventilation fan is operated, and pollution in the bathroom may occur due to breeding of the molds and the bacteria. Accordingly, the bathroom may be prevented from becoming a habitat for molds and bacteria by promptly removing moisture on a floor or walls of the bathroom, and drying wet bath and toilet appliances, such as wet towels.

Further, various facilities such as washstand, toilet, mirror, towel rack, toothbrush holder as well as a storage room that store various bath and toilet items, including towels, may be installed at the bathroom. Meanwhile, a user may use electronic products, such as hair dryers and shavers, and personal items, such as make up, in the bathroom. Thus, if a bathroom management apparatus (e.g., a bathroom cabinet on a wall or floor surface) integrating a function of a toothbrush sterilizer, a function of a cosmetics refrigerator, and a charging function of the electronic products, along with providing a storage function and a bathroom drying function is developed, the space utility of the bathroom may be increased.

Furthermore, if a bath management apparatus was designed to selectively include various functional modules, such as a storage module having a storage function, an air conditioning module having a bathroom drying function, a sterilizing module functioning as a toothbrush sterilizer, a refrigerating module functioning as a cosmetics refrigerator, and a charging module functioning to charge the electronic products, the user may select desired modules from the function modules to include in the bath management apparatus. Accordingly, a bathroom management apparatus designed to firmly support a weight of one or more of the function modules is desirable. Furthermore, when one of the installed function modules fails (e.g., is accidentally exposed to water), the bathroom management apparatus should be designed to enable the function module to be easily repaired or replaced.

BRIEF DESCRIPTION OF THE DRAWINGS

The embodiments will be described in detail with reference to the following drawings in which like reference numerals refer to like elements, and wherein.

DETAILED DESCRIPTION

Hereinafter, a bathroom management apparatus according to embodiments of the present disclosure will be described in detail with reference to the accompanying drawings.

Figure 1:
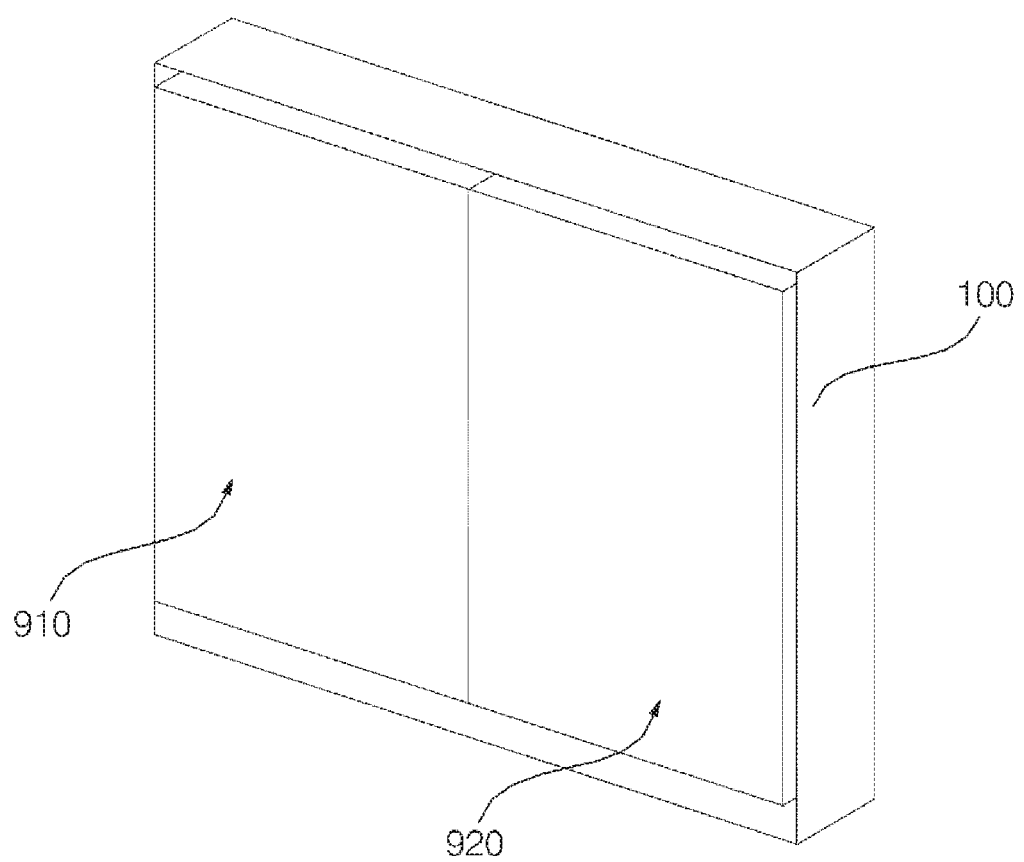
FIG. 1 is a combined perspective view showing a bathroom management apparatus according to an embodiment of the present disclosure.
Figure 2:
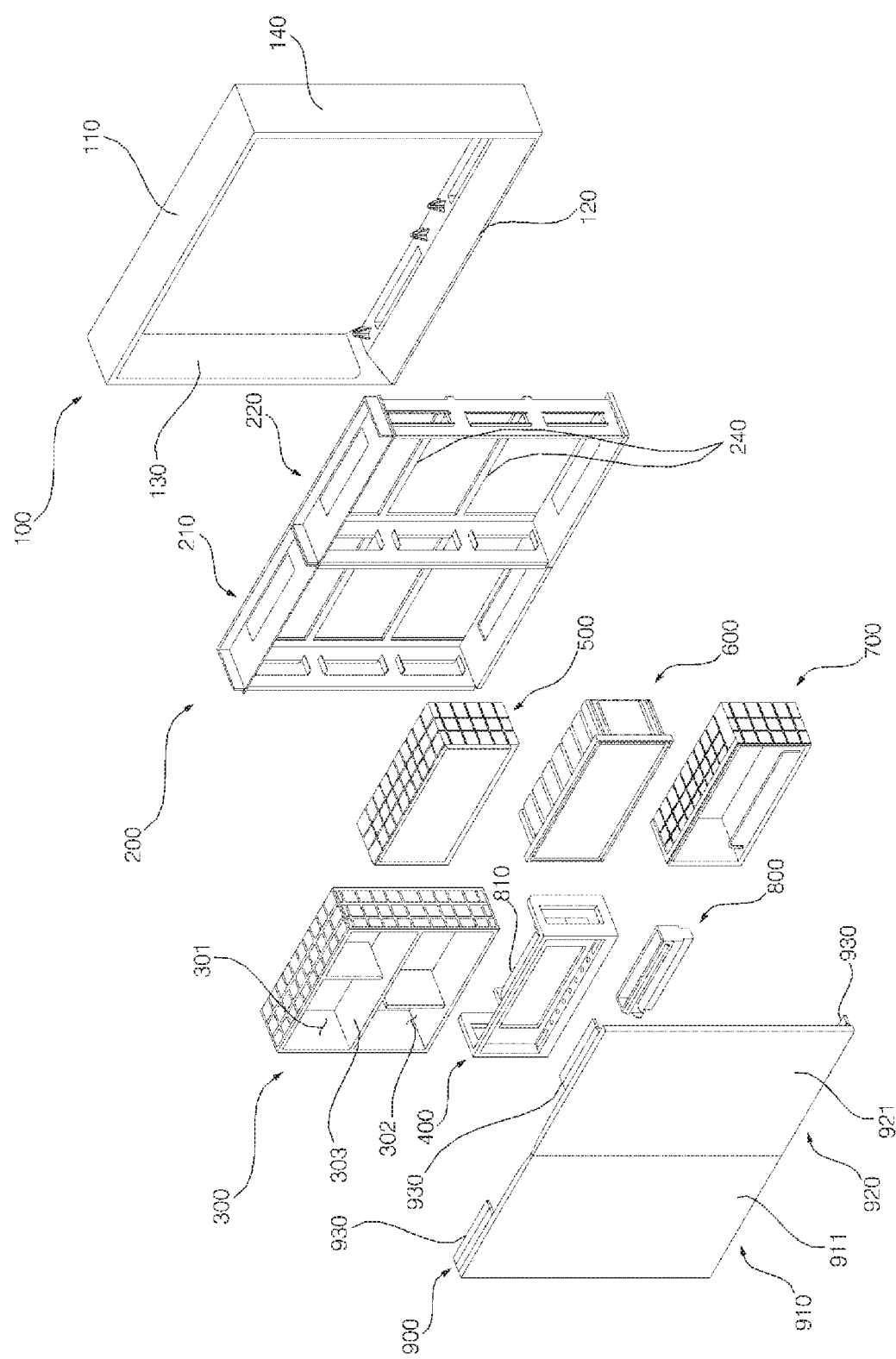
FIG. 2 is an exploded perspective view showing a bathroom management apparatus according to an embodiment of the present disclosure.

FIG. 1 is a combined perspective view showing a bathroom management apparatus according to a first embodiment of the present disclosure, and FIG. 2 is an exploded perspective view showing a bathroom management apparatus according to a first embodiment of the present disclosure. Referring to FIG. 1 and FIG. 2, the bathroom management apparatus (also referred to as a bathroom wall cabinet or medicine cabinet) according to a first embodiment of the present disclosure may include a cabinet 100, a frame 200 installed inside the cabinet 100, a plurality of function modules 300, 400, 500, 600, 700, and 800, and a door 900 (or doors 910, 920) provided in a forward direction of the cabinet 100 (e.g., opposite to a wall where the cabinet 100 is installed).

The cabinet 100 may have a substantially hollow structure and have a substantially square or rectangular shape of which a front surface and a rear surface are open. Thus, the cabinet 100 may form an upper external appearance, a lower external appearance, a left external appearance, and a right external appearance. The cabinet 100 may include an upper panel 110 forming an upper side surface, a lower panel 120 forming a lower side surface, a left side panel 130 forming a left side surface, and a right side panel 140 forming a right side surface.

The upper panel 110 may connect a top end of the left side panel 130 with a top end of the right side panel 140. The lower panel 120 may connect a bottom end of the left side panel 130 with a bottom end of the right side panel 140. A left end of the upper panel 110 may be coupled with a top end of the left side panel 130, and a right end of the upper panel 110 may be coupled with a top end of the right side panel 130. Further, a left end of the lower panel 120 may be coupled with a lower end of the left side panel 130, and a right end of the lower panel 120 may be coupled with a bottom end of the right side panel 140.

The frame 200 may include frame bodies 210 and 220 having a substantially square or rectangular shape corresponding to the cabinet 100 of which a front surface and a rear surface are open, and back brackets (or back brace) 240 provided in a rearward direction of the frame bodies 201 and 220 to be coupled with rear surfaces of the frame bodies 210 and 220. The frame bodies 210 and 220 may reinforce a stiffness of the cabinet 100. The bracket 240 may be thicker than the frame bodies 210 and 220 to reinforce the stiffness of the frame bodies 210 and 220.

The frame bodies 210 and 220 may provide at least one space in which the function modules 300, 400, 500, 600, 700, and 800 are installed. The function modules 300, 400, 500, 600, 700, and 800 may include, for example, a towel care module 300, a sterilizing module 400, a secret box module (or safe) 500, a refrigerating module 600, a charging module 700, and a blower out (or air output) module 800. The towel care module 300, the sterilizing module 400, the secret box module 500, the refrigerating module 600, the charging module 700, and the blower out module 800 may be independently provided and installed inside the frame bodies 210 and 220. Ribs may protrude from upward, downward, left, and/or right sides of the function modules 300, 400, 500, 600, 700, and 800, respectively. The ribs protruding from left and right sides or other sides of the function modules 300, 400, 500, 600, 700, and 800 may be supported by an inner rib 215 to be described later protruding in the frame bodies 210 and 220.

The towel care module 300 may include a function division plate (or horizontal plate) 303. The function division plate 303 extends horizontally to vertically divide an inner space of the towel care module 300. The towel care module 300 may be formed with a first storage space 301 to store towels (or other items) at above the function division plate 303 and may be formed with a second storage space 302 to store the towels (or other items) below the function division plate 303. As described below, the towel care module 300 may dry and warm the stored towels (or other stored items). The towel care module 300 may include a first independent towel care module having only the first storage space 301 without the function division plate 303 and a second independent towel care module having only the second storage space 302.

The sterilizing module 400 may be used to sterilize a toothbrush or other bathroom item. For example, the sterilizing module 400 may receive one or more toothbrushes, and may include a lamp that irradiates sterilizing ultraviolet rays toward the stored toothbrushes.

The blower out module 800 may be installed below the sterilizing module 400. An air conditioning module (or dryer module) 810 may including a blower (or fan) that sucks in and blows air to the blower out module 800 and a heater that heats the air blown from the blower, and the air conditioning module 810 may be installed at rearward of the sterilizing module 400 and corresponding to a top side of the blower out module 800 so that the sterilizing module 400 and the air conditioning module 810 may be integrally formed. The blower out module 800 may exhaust the air blown from the blower into an interior of the bathroom.

The secret box module 500 may be used to store objects out of view of a user, such as to store objects within an enclosed or locked space. Thus, the secret box module 500 may help prevent the stored objects from being seen or touched by children and visitors.

The refrigerating module 600 may be used as usage to cool medicines and cosmetics. The refrigerating module 600 may be installed adjacent to or otherwise coupled to a thermoelectric module that supplies cold air into the refrigerating module 600 and/or emits warm air outside of the refrigerating module 600.

The charging module 700 may be used to charge electronic devices, such as a hair dryer and an electric shaver. The charging module 700 may include a holder that receives the hair dryer and a receptacle to receive a power plug of the electronic device or a power plug of a charger that charges the electronic device.

Two frame bodies 210 and 220 may be provided and may be horizontally oriented such that the first frame body 210 is positioned within the cabinet 100 and the second frame body 220 is provided at one side of the first frame body 210 within the cabinet 100. The first frame body 210 and the second frame body 220 have a substantially same structure, shape, and/or size.

The desired modules received in the first frame body 210 and the second frame body 220 may be customized based on user need. For example, the towel care module 300, the sterilizing module 400, the secret box module 500, the refrigerating module 600, the charging module 700, and the blower out module 800 may be selected and installed according to a need of a consumer. In another example, only a plurality of towel care modules 300 may be installed, or alternatively, two towel care modules 300 and one refrigerating module 600 may be installed in the frame bodies 210 and 220. According to the number of towel care modules 300, the sterilizing modules 400, the secret box modules 500, the refrigerating modules 600, and the charging modules 700 installed in the frame bodies 210 and 220, one or more frame bodies 210 and 220 may be provided. Although two frame bodies 210 and 220 are shown in the drawings, fewer, different, or more two frame bodies 210 and 220 may be installed in order to enable different combinations of modules 300, 400, 500, 600, 700, and 800 to be received in the cabinet 100.

The door 900 may form a front external appearance of the bathroom management apparatus. The door 900 may open/close an open front surface of the cabinet 100. In one example, a quantity of doors 900 provided in front of the cabinet 100 may correspond to a quantity of the frame bodies 210 and 220 inserted in the cabinet 100. In a first embodiment, since the two frame bodies 210 and 220 are provided, two doors 900 are provided, including a first door 910 and a second door 920. The first door 910 may be provided in a forward direction of the first frame body 210 and may open a left side of an open front surface of the cabinet 100, and the second door 920 may be provided in a forward direction of the second frame body 220 and may open a right side of an open front surface of the cabinet 100.

Mirrors 911 and 912 may be provided at front surfaces of the first door 910 and the second door 920, respectively. The mirrors 911 and 921 may be used instead of a mirror inside the bathroom. The mirrors 911 and 921 include a first mirror 911 provided at a front surface of the first door 910 and a second mirror 921 provided at a front surface of the second door 920.

A hinge 930 may be installed at a rear surface of the door 900. The hinge 930 may include a first hinge member (or hinge surface) having one end that is coupled to a rear surface of the door. The hinge 930 may further include a second hinge member (or second hinge surface) having one end that is rotatably coupled to an opposite end of the first hinge member and an opposite end that is rotatably coupled with the frame bodies 210 and 220. The hinges 930 may be installed at a top side and a lower side of a rear surface of the first door 910, respectively, may be installed at a top side and a bottom side of a rear side of the second door 910.

Figure 3:
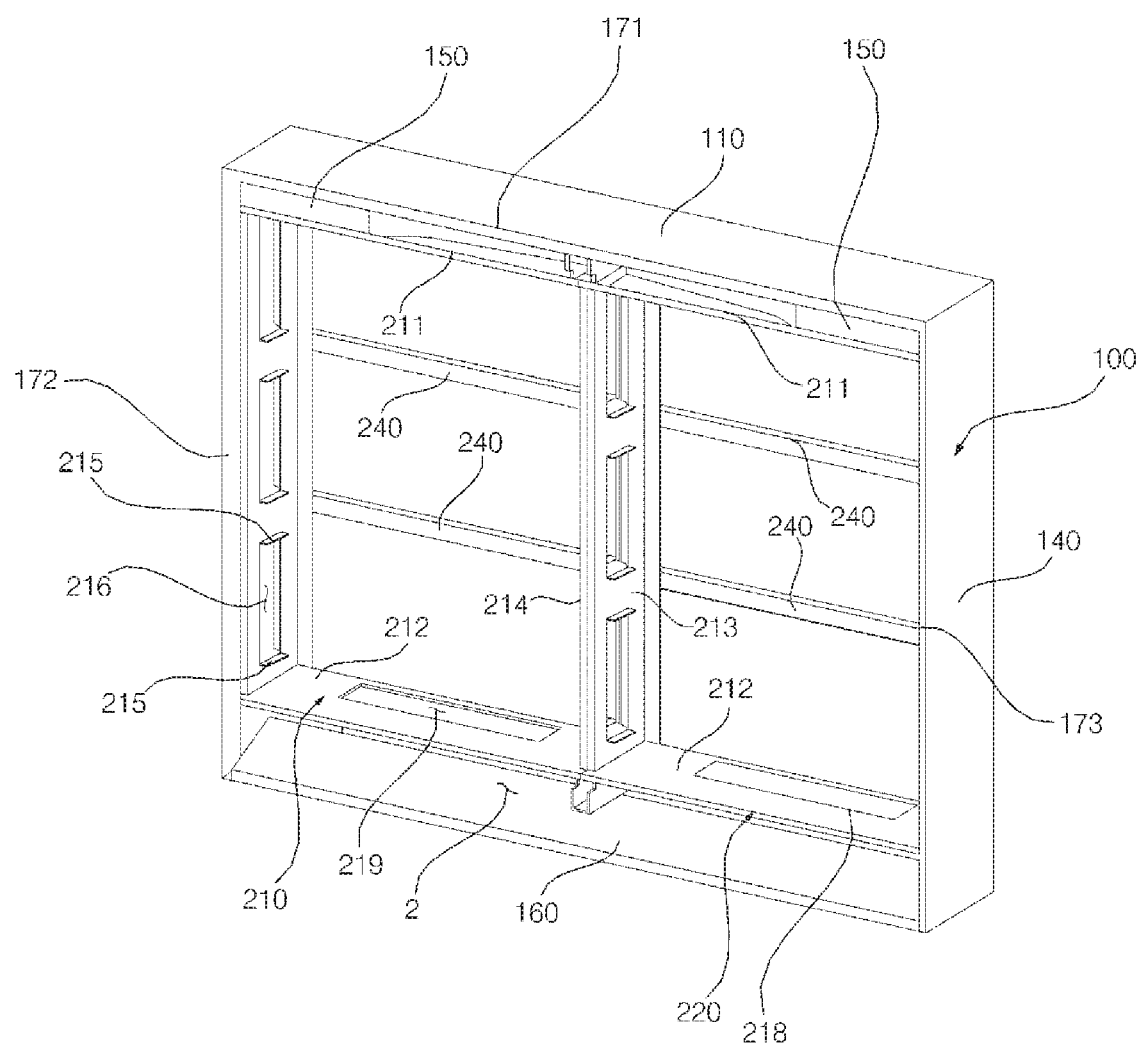
FIG. 3 is a view illustrating a coupled state between the cabinet and the frame shown in FIG. 3.
Figure 4:
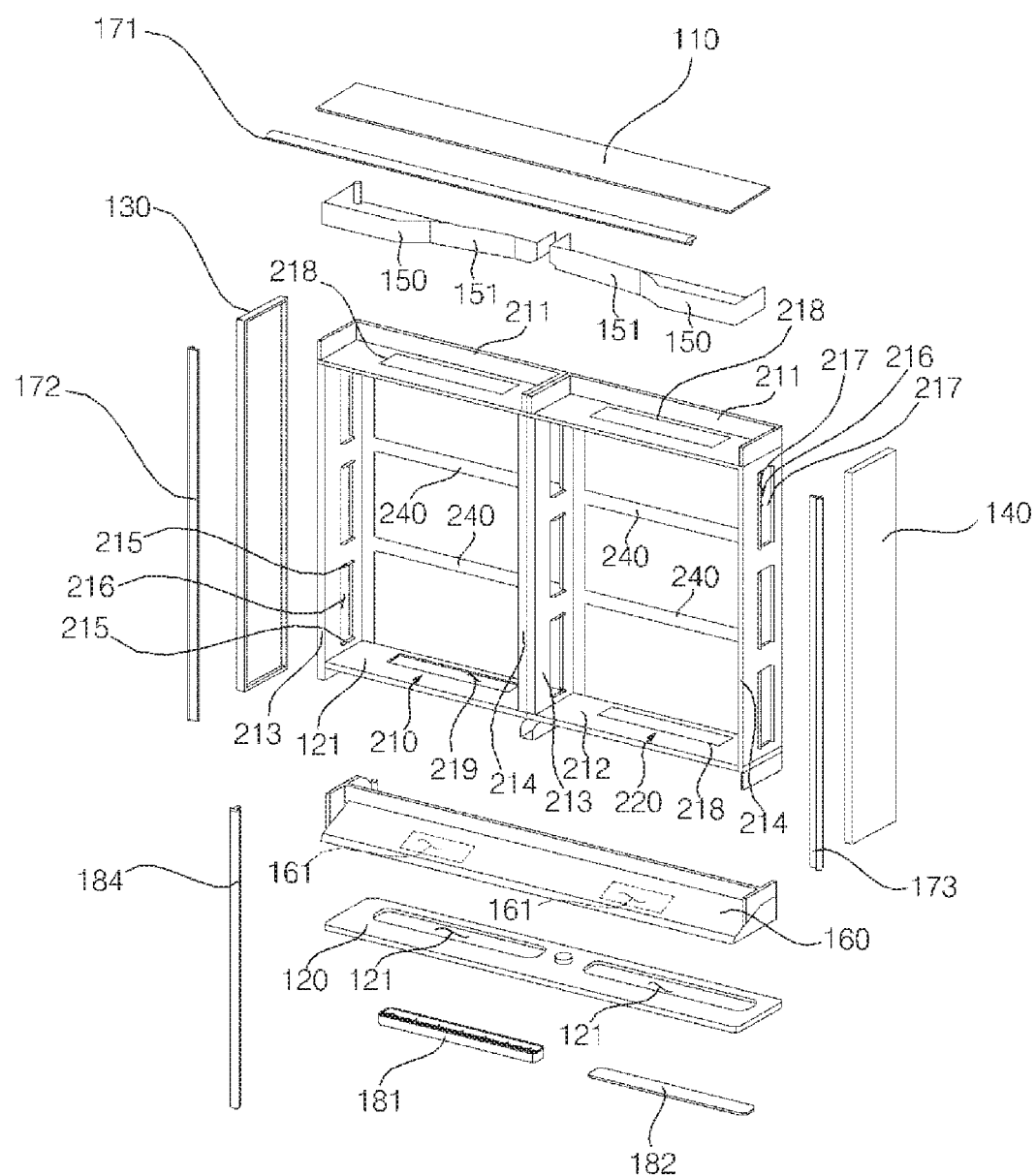
FIG. 4 is an exploded perspective view of FIG. 3.

FIG. 3 is a view illustrating a coupled state between the cabinet and the frame shown in FIG. 3, and FIG. 4 is an exploded perspective view of FIG. 3. Referring to FIG. 3 and FIG. 4, top surfaces and bottom surfaces of frame bodies 210 and 220 may be spaced apart from a cabinet 100. That is, the top surfaces of the frame bodies 210 and 220 may be spaced apart from the upper panel 110 of the cabinet 100 downward, and the bottom surfaces of the frame bodies 210 and 220 are spaced apart from the lower panel 110 of the cabinet 100 upward.

An upper cover 150 may be provided at a space between the upper panel 110 of the cabinet 100 and the top surfaces of the frame bodies 210 and 220. The upper cover 150 may be inserted into the space between the upper panel 110 of the cabinet 100 and the top surfaces of the frame bodies 210 and 220 to be coupled with the upper panel 110 of the cabinet 100 and the top surfaces of the frame bodies 210 and 220.

When a door 900 is closed, the upper cover 150 may cover the space between the upper panel 110 of the cabinet 100 and the top surfaces of the frame bodies 210 and 220, a hinge 930 may be installed at a rear top side of the door 900 is not viewed from a rear direction of the bathroom management apparatus through a space between the upper panel 110 and top surfaces of the frame bodies 210 and 220. When the door 900 is open, the upper cover 150 may be positioned to block or otherwise prevent the bathroom wall from being viewed from the forward direction of the bathroom management apparatus through a space between the upper panel 110 and the top surface of the frame bodies 210 and 220.

The upper cover 150 may have a shape having open top and rear surfaces and having a bottom surface, a front surface, a left surface, and a right surface.

A concave groove 151 to receive a hinge 930 when the door 900 is closed may be formed at the front surface of the upper cover 150 so that a space for receiving the hinge 930 may be formed between the upper panel 110 and the top surfaces of the frame bodies 210 and 220.

Further, a control panel (or user interface) 160 may be inserted between the lower panel 120 of the cabinet 100 and bottom surfaces of the frame bodies 210 and 220. The control panel 160 may be inserted between the lower panel 120 of the cabinet 100 and bottom surfaces of the frame bodies 210 and 220 and may be coupled with the lower panel 120 of the cabinet 100 and the bottom surfaces of the frame bodies 210 and 220.

Remaining regions of the control panel 160, except for a top side coupled with the bottom surfaces of the frame bodies 210 and 220, may be spaced apart from the bottom surfaces of the frame bodies 210 and 220. Air exhausted from the blower out module 800 may be moved into a first air outlet 2 to be described later through a space between bottom surfaces of the frame bodies 210 and 220 and a top side of the control panel 160. After the user showers, the user's body may be dried using air exhausted into the bathroom from the first air outlet 2.

A user interface as well as an input unit for controlling function modules 300, 400, 500, 600, 700, 800, and 810 may be installed at the control panel 160. The input unit may include at least one of a button and a touch screen, and the user may push or touch the input unit to operate or stop the function modules 300, 400, 500, 600, 700, 800, and 810. In one example, an installed region of the input unit of the control panel 160 may be exposed at position corresponding to a lower portion of the door 900 when the door 900 is closed.

Meanwhile, the cabinet 100 may include decoration members (or decoration panels) 171, 172, and 173 coupled with a front end of the upper panel 110, a front end of the left side panel 130, and a front end of the right side panel 140, respectively. The decoration members 171, 172, and 173 may include a first decoration member 171 coupled with a front end of the upper panel 100, a second decoration member 172 coupled with a front end of the left side panel 130, and a third decoration member 173 coupled with a front end of the right side panel 140. In another example, the decoration members 171, 172, and 173 may not be installed at a front end of the lower panel 120 and the front end of the lower panel 120 may be covered by a front end of the control panel 160. That is, the control panel 160 may also perform a function of the decoration members 171, 172, and 173 by covering the front end of the lower panel 120. It is preferred that the control panel 160 is formed with the same color and material as those of the decoration members 171, 172, and 173.

The frame bodies 210 and 220 may include an upper frame (or upper frame surface) 211 forming an upper side, a lower frame (or lower frame surface) 212 forming a lower side, and a left side frame (or left frame surface) 213 forming a left side, and a right side frame (or right frame surface) 214 forming a right side. The upper frame 211 may connect a top end of the left side frame 213 with a top end of the right side frame 214. The lower frame 212 may connect a bottom end of the left side frame 213 with a bottom end of the right side frame 214.

A left end of the upper frame 211 may be coupled with a top end of the left side frame 213, and a right end of the upper frame 211 may be coupled with a top end of the right side frame 214. Further, a left end of the lower frame 212 may be coupled with a bottom end of the left side frame 213, and a right end of the lower frame 212 may be coupled with a bottom end of the right side frame 214.

The upper frame 211 and the lower frame 212 have a similar structure. The left side frame 213 and the right side frame 214 have a similar structure. Accordingly, the frame body 210 and the second frame body 220 may be installed inside the cabinet 100 regardless of upper and lower sides and regardless of left and right sides.

The upper frame 211 may have a shape of which a top surface and a front surface are open and may include a bottom surface, a left surface, a right surface, and a rear surface. Further, the lower frame 212 may have a shape the correspond to shape of the upper frame 211 that is flipped upside down, such that the lower frame has a shape of which a bottom surface and a front surface are open. That is, the lower frame 212 may include a left surface, a right surface, and a rear surface.

First opening portions (or first openings) 216 having a square shape may be formed in the left side frame 213 and the right side frame 214, respectively. The first opening portion 216 may form a path through which wires of the function modules 300, 400, 500, 600, 700, and 800 pass. The quantity of the first opening portions 216 included in the frame 200 may correspond to number of the function modules 300, 400, 500, 600, 700, and/or 800 installed inside the frame bodies 210 and 220. In another example, additional or fewer first opening portions 216 may be present, such as to have an unused first opening portion 216 to install two or more modules in a single first opening portion 216.

Inner ribs 215 may be formed at inner sides of the left side frame 213 and the right side frame 214, respectively. The inner ribs 215 may protrude to the inner sides of the frame bodies 210 and 220 from a top side and a bottom side of the first opening portion 216.

The inner rib 215 may guide insertion of the function modules 300, 400, 500, 600, 700, and 800 when the function modules 300, 400, 500, 600, 700, and 800 are individually inserted into the frame bodies 210 and 220. After the function modules 300, 400, 500, 600, 700, and 800 are inserted into the frame bodies 210 and 220, the inner rib 215 may support the function modules 300, 400, 500, 600, 700, and 800.

Outer ribs 217 may be formed at outer sides of the left side frame 213 and the right side frame 214, respectively. The outer ribs 217 may protrude to the outside of the frame bodies 210 and 220 from a front side and a rear side of the first opening portion 216, respectively.

The outer ribs 217 may be spaced a part from each other in forward and reward directions while interposing the first opening portion 216 therebetween to form a path through which wires of the function modules 300, 400, 500, 600, 700, and 800 pass after the wires of the function modules 300, 400, 500, 600, 700, and 800 pass through the first opening portion 216.

Cut lines 218 having a square shape may be formed at a bottom surface of the upper frame 211 and a top surface of the lower frame 212, respectively. The cut lines 218 may be formed by partially cutting a bottom surface of the upper frame 211 and a top surface of the lower frame 212 so that a user may easily separate an inner region divided by the cut lines 218 from a bottom surface of the upper frame 211 in a top surface of the lower frame 212.

When the sterilizing module 400 is installed close to the upper frame, the user may use the cut line 218 formed at the upper frame 211, among the cut line 218 formed at the upper frame 211 and the cut line 218 formed at the lower frame 212, to separate an inner region of the upper frame 211 divided by the cut line 218. When the sterilizing module 400 is installed close to the lower frame, the worker may use the cut line 218 formed at the lower frame 211 among the cut line 218 formed at the upper frame 211 and the cut line 218 formed at the lower frame 212 to separate an inner region of the lower frame 212 divided by the cut line 218.

The second opening portions (or second openings) 219 may be formed at the upper frame 211 and the lower frame 212 when the inner region divided by the cut line 218 is separated by the worker. Further, a third opening portion (or third openings) 161 may be formed at a lower side of the second opening portion 219 in a lower side of the control panel 160. Further, a fourth opening portion 121 may be formed at a lower side of the third opening portion 161 in a lower panel 120 of the cabinet 100.

A blower louver 181 may be installed at a region corresponding to the fourth opening portion 121, or a lower cover 182 may be installed in the top surface of the lower panel 120. When the fourth opening portion 121 is located under the sterilizing module 400, the lower louver 181 may be installed at a region corresponding to the fourth opening portion 121 in the lower panel 120. Otherwise, a lower cover 182 may be installed at a region corresponding to the fourth opening portion 121 in the lower panel 120 so that the fourth opening portion 121 is shielded by the lower cover 182.

Figure 8:
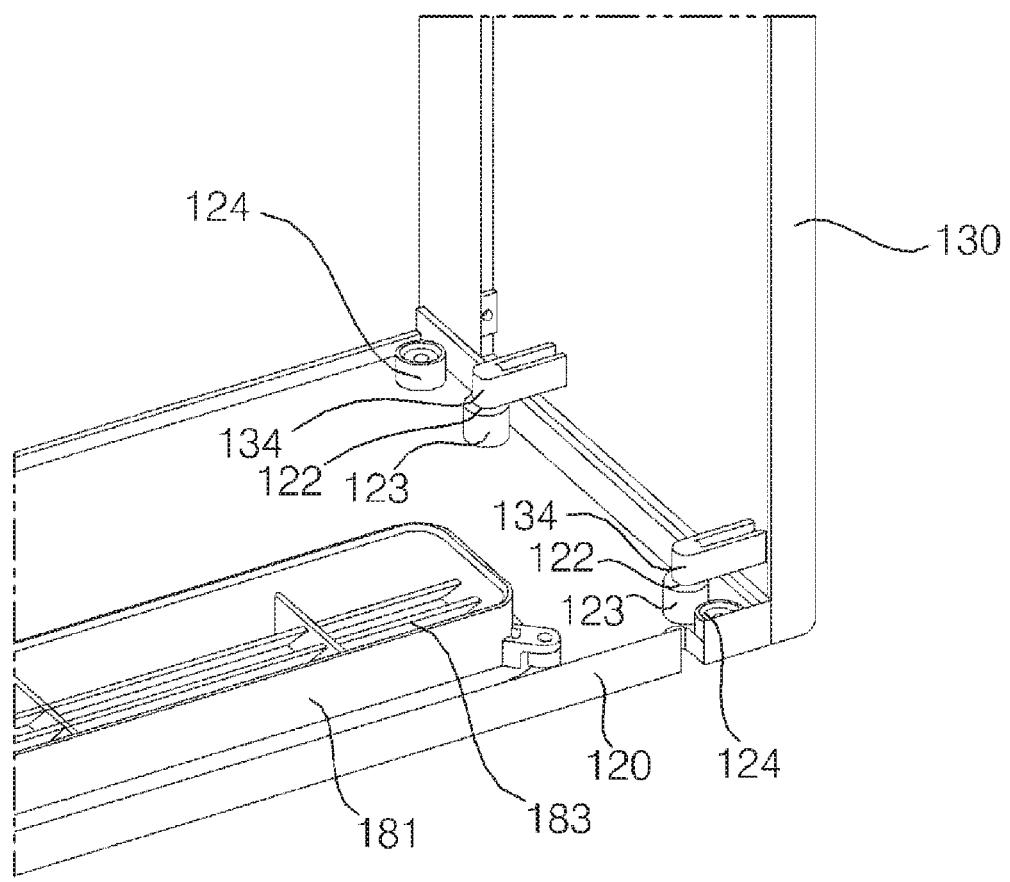
FIG. 8 is a rear perspective view illustrating a lower panel and a left side panel shown in FIG. 4.

As shown in FIG. 8, the blower louver 181 may include a discharge grill 183, and may be installed at a region corresponding to the fourth opening portion 121 in the lower panel 120 to guide air from the blower out module 800 into the fourth opening portion 121. When the blower louver 182 is installed at a region corresponding to the fourth opening portion 121 in the lower panel 120, the fourth opening portion 121 may be referred to as a second air outlet 121. That is, in the cabinet 100, the first air outlet 2 may be spaced apart from a lower frame 212 being a bottom surface of the frame 200, and a second air outlet 121 is formed at a bottom surface of the frame 200.

The blower out module 800 may be provided inside the control panel 160 between the lower panel 120 and the lower frame 212. Further, a top end of the blower out module 800 may be inserted into the second opening portion 219 so that the blower out module 800 sucks air blown from the blower, and a bottom end of the blower out module 800 is connected to the blower louver 181 through the third opening portion 161. Moreover, a front opening portion communicating with the first air outlet 2 may be formed at a front surface of the blower out module 800.

Since the blower out module 800 may be installed therein with a motor and a fluid path switching vane rotated by a driving force of the motor, the fluid path switching vane may be rotated by the driving force of the motor to open the front opening portion and close a bottom end such that air sucked from an air conditioning module 810 passes through the front opening portion and is discharged into the bathroom through the first air outlet 2. When the front opening portion is closed and the bottom end is open, the air sucked from the blower passes through the blower louver 181 and is discharged into the bathroom through the second air outlet 121. That is, the blower out module 800 switches the air blown from the air conditioning module 810 to one of the first air outlet 2 and the second air outlet 121.

A user may control a rotation position of the fluid path switching vane of the blower out module 800 by operating the input unit installed at the control panel 160 to discharge air into the bathroom through the first air outlet 2 or to discharge the air into the bathroom through the second air outlet 121. The air discharged into the bathroom through the first air outlet 2 may be used to dry the user's body. The air discharged into the bathroom through the second air outlet 121 may be used to dry an interior of the bathroom.

Meanwhile, when a plurality of frame bodies 210 and 220 are provided, a center cover 184 may be further installed at front surfaces of adjacent side frames 214 and 213 of the plurality of frame bodies 210 and 220. That is, in certain embodiment, two frame bodies 210 and 220 may be provided, and center covers 184 may be installed at a front surface of the right side frame 214 of the first frame body 210 and a front surface of a left side frame 213 of the second frame body 220, respectively. The center cover 184 may cover the right side frame 214 of the first frame body 210 and the left side frame 213 of the second frame body 220 in a forward direction. In addition, after the function modules 300, 400, 500, 600, and 700 are inserted into the frame bodies 210 and 220, the center cover 184 may protrude toward both sides of the function modules 300, 400, 500, 600, and 700 to cover a module locking rib (not shown)

locked at a front surface of the both side frames 213 and 214 of the frame bodies 210 and 220.

Figure 5:
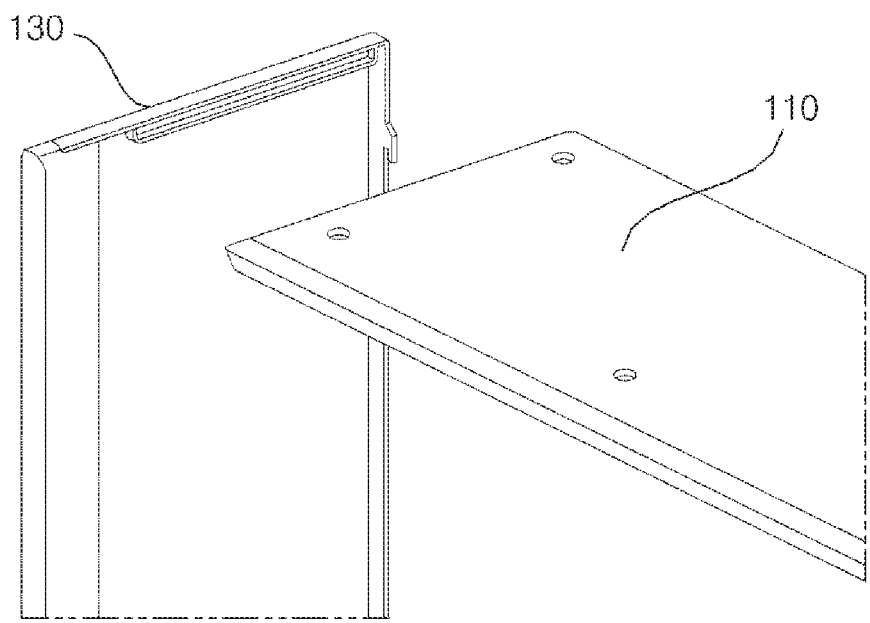
FIG. 5 is a right perspective view illustrating an upper panel and a left side panel shown in FIG. 4.
Figure 6:
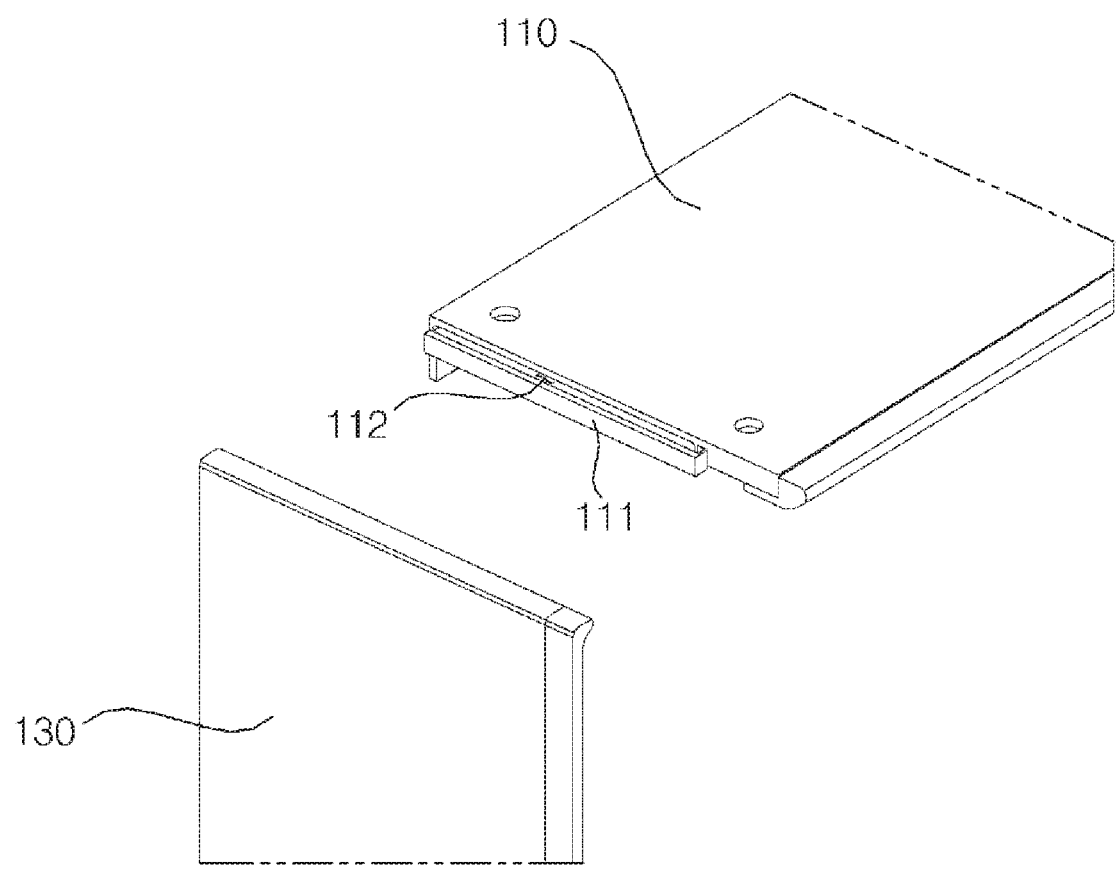
FIG. 6 is a left perspective view illustrating an upper panel and a left side panel shown in FIG. 4.
Figure 7:
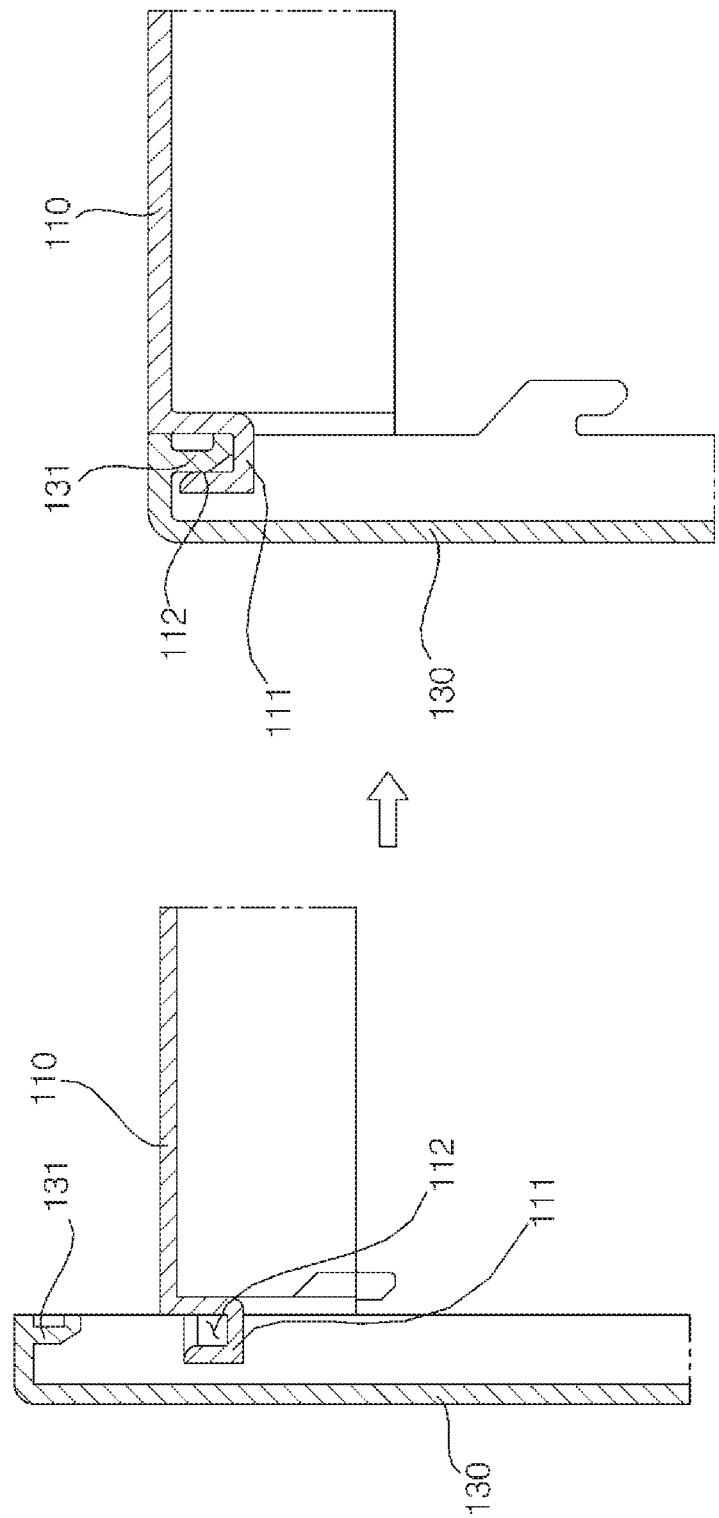
FIG. 7 is a sectional view illustrating a process of coupling the upper panel with the left side panel shown in FIG. 5 and FIG. 6.

Hereinafter, a process of manufacturing the cabinet 100 will be described with reference to FIG. 5 to FIG. 8. FIG. 5 is a right perspective view illustrating an upper panel and a left side panel shown in FIG. 4, FIG. 6 is a left perspective view illustrating an upper panel and a left side panel shown in FIG. 4, FIG. 7 is a sectional view illustrating a process of coupling the upper panel with the left side panel shown in FIG. 5 and FIG. 6, and FIG. 8 is a rear perspective view illustrating a lower panel and a left side panel shown in FIG. 4.

Referring to FIG. 5 to FIG. 8, first end ribs 111 having first end grooves 112 at top sides thereof may be formed at both ends of the upper panel 110, respectively. The first end ribs 111 may protrude to both end sides of the upper panel to have a square shape. The first end groove 112 may have a square shape that correspond to that of the first end rib 111. Although FIG. 9 to FIG. 12 only show the first end rib 111 that is formed at a left end of the upper panel 110, this first end rib 111 or another first end rib 111 may be formed at the right end of the upper panel 110.

Moreover, second end ribs 131 that are inserted into the first end grooves 112 may be formed an inner side of the left side panel 130 and an inner side of the right side panel 140, respectively. The second end rib 131 may protrude from an inner top side of the left side panel 130 downward to have a square shape. Although FIG. 9 to FIG. 12 show only the second end rib 131 formed at a top end of the left side panel 130, the second end rib 131 may be formed at a top end of the right side panel 140. The second end rib 131 may slide the left side panel 130 and the right side panel 140 to be inserted into the first end groove 112 at a top side of the first end rib 111, to couple a top end of the left side panel 130 with a left end of the upper panel 110, and to couple a top end of the right side panel 140 with a right end of the upper panel 110.

Furthermore, third end ribs 123 having second end grooves 122 at top sides thereof may be formed at both top ends of the lower panel 120, respectively. A pair of third end ribs 123 may have a circular shape and may be spaced apart from each other forward and rearward at both ends of the lower panel 120. The second end groove 122 may have a similar circular shape as that of the third end rib 123. Although FIG. 9 to FIG. 12 show that the third end rib 123 is formed at a left top side of the lower panel 120, this or another third end rib 123 may be formed at the right top side of the lower panel 120.

Furthermore, fourth end ribs 134 inserted into the second end grooves 122 may be formed at an inner side of the left side panel 130 and an inner side of the right side panel 140. The fourth end rib 134 protrudes a direction perpendicular to an inner side of the left side panel 130 and an inner side of the right side panel 140 and an end of the fourth end rib 134 may have a shape that bent downward substantially at 90°, and an end of the fourth end rib 134 may be inserted into the second end groove 122. Although FIG. 9 to FIG. 12 only show the fourth end rib 134 that is formed at a bottom end of the left side panel 130, this or another fourth end rib 134 as the fourth end rib 134 formed at a bottom end of the left side panel 130 is formed at a bottom end of the right side panel 140.

The fourth end rib 134 may slide the left side panel 130 and the right side panel 140 to be inserted into the second end groove 122 at a top side of the third end rib 123, to couple a bottom end of the left side panel 130 with a left end of the upper panel 120, and to couple a bottom end of the right side panel 140 with a right end of the lower panel 120.

As described above, since the left side panel 130 and the right side panel 130 are coupled with the upper panel 110 and the lower panel 120 in a upward and downward sliding scheme, various function modules 300, 400, 500, 600, 700, 800, and 810 may be installed inside the frame 200 fail, in a state that the bathroom management apparatus is installed on a bathroom wall, the left side panel 130 and the right side panel 140 slide upward to be separated, the function modules 300, 400, 500, 600, 700, 800, and 810 are easily separated from the frame 200 to be repaired.

Meanwhile, referring to FIG. 8, the lower panel 120 may be further formed therein with a locking rib 124 which is locked with a third locking boss 163 formed at a control panel 160 through a screw. That is, the third locking boss 163 may be locked with the locking rib 124 through the screw so that the control panel 160 is coupled with the lower panel 120.

Figure 9:
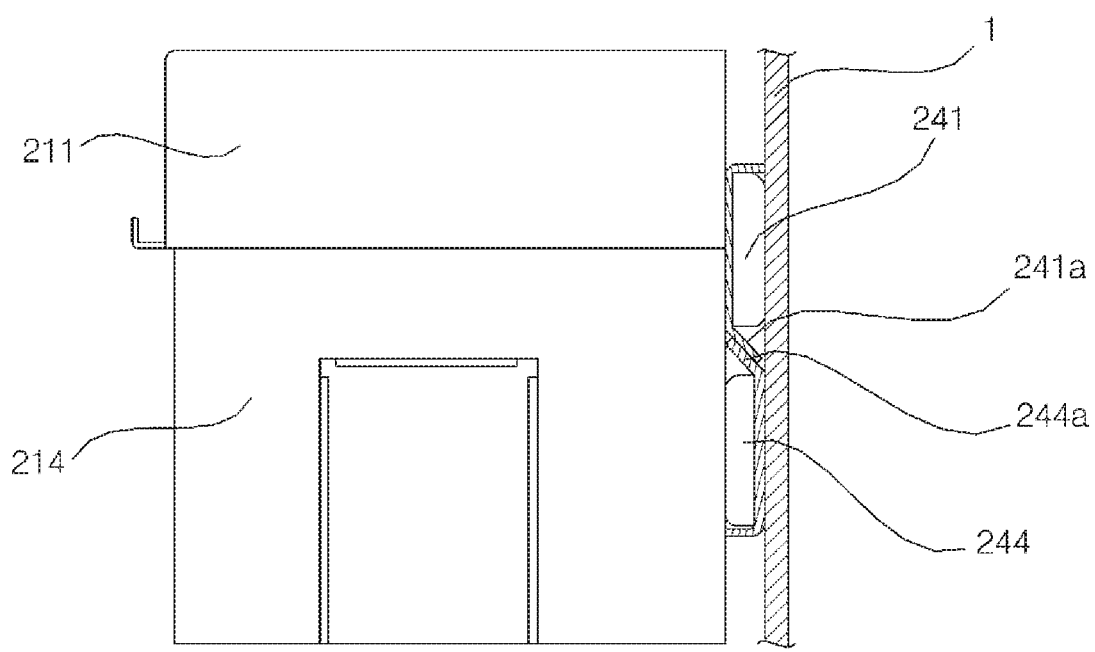
FIG. 9 is a side sectional view illustrating a state that the bathroom management apparatus according to an embodiment of the present disclosure is installed on a bathroom wall.
Figure 10:
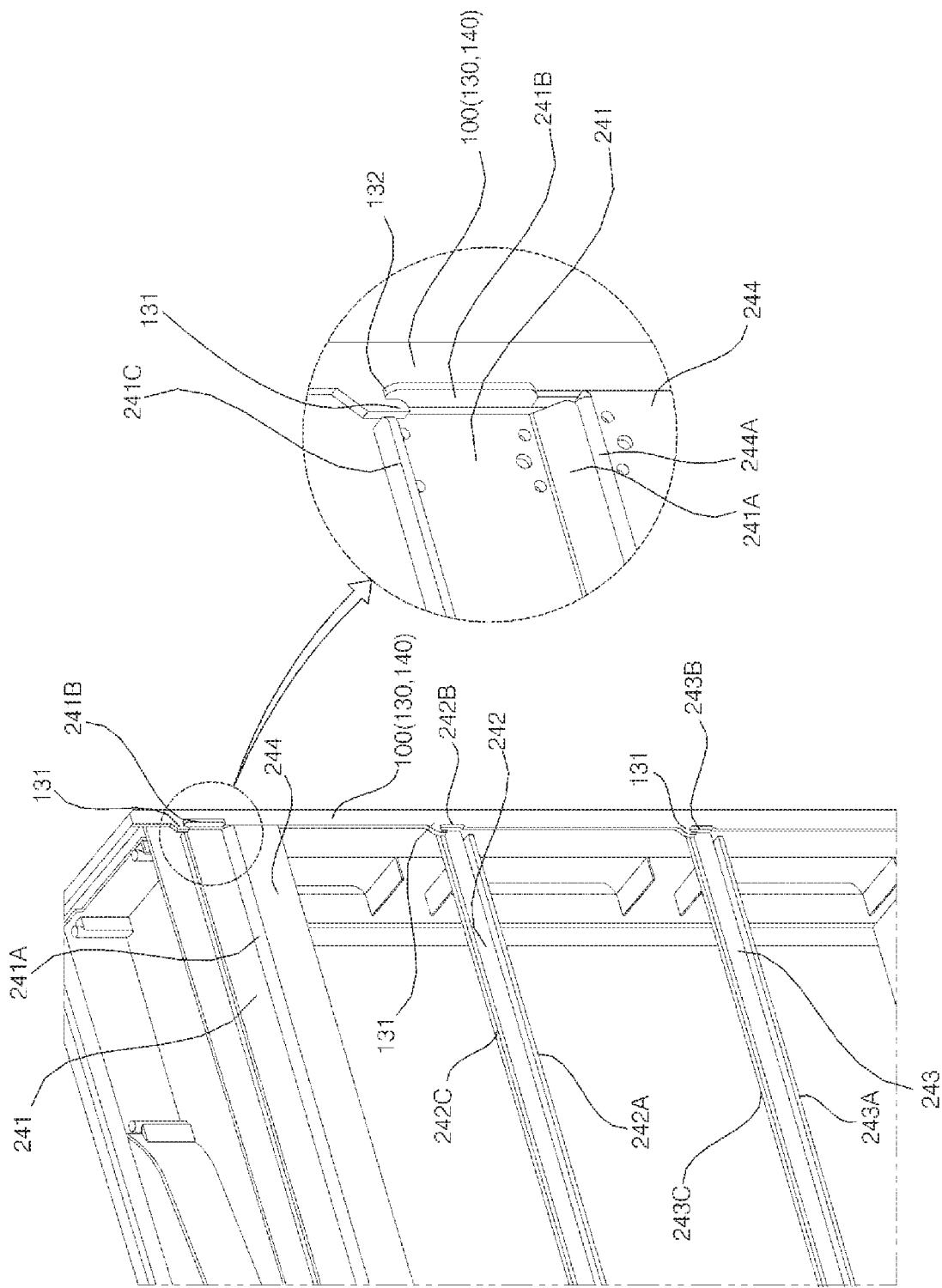
FIG. 10 is a partially rear perspective view of FIG. 3.

FIG. 9 is a side sectional view illustrating a state that the bathroom management apparatus according to an embodiment of the present disclosure is installed on a bathroom wall, and FIG. 10 is a partially rear perspective view of FIG. 3. Referring to FIG. 9 and FIG. 10, a back bracket 240 may be longitudinally formed rightward and leftward. The back bracket 240 may be coupled with the left side frame 213 and the right side frame 214 of the first frame body 210 and the left side frame 213 and the right side frame 214 of the second frame body 220 to connect the first frame body 210 with the second frame body 220. A left end of the back bracket 240 may be coupled with a rear surface of the left side frame 213 of the first frame body 210, and a right end of the back bracket 240 is coupled with a rear surface of the right side frame 214 of the first frame body 220. The back bracket 240 may include an upper back bracket 241 located at the upper most side and lower back brackets 242 and 243 located at the lower most side. In certain embodiments, two lower back brackets 242 and 243 may be vertically spaced apart from each other.

A length of the back bracket 240 may be determined according to the number of frame bodies 210 and 220. That is, when one of frame bodies 210 and 220 is used, the back bracket 240 may be designed to have a relatively shorter length. When two or more frame bodies 210 and 220 are used, the back bracket 240 may have a relatively longer length.

Meanwhile, a mounting bracket 244 for mounting the bathroom management apparatus may be provided at a wall of the bathroom. The mounting bracket 244 may have a structure that is similar to that of the upper back bracket 241 to support the upper back bracket 241. That is, an upside down copy of the upper back bracket 214 may be used as a mounting bracket 244.

A first inclined part (or first inclined surface) 244A may be inclined toward a top end of the mounting bracket 244 to protrude in a forward direction upward. A second inclined part (or second inclined surface) 241A may be inclined toward a bottom end of the upper back bracket 241 to protrude in a rearward direction downward. In a state that the mounting bracket 244 is installed on a bathroom wall 1, the first inclined part 241A may be inserted into a space between the first inclined part 244A and the bathroom wall 1 to be supported at the first inclined part 244A so that the bath management apparatus may be installed on the bathroom wall 1.

Meanwhile, side bending parts (or side bending extensions) 241B, 242B, and 243B may be formed at both ends of the upper back bracket 241 and the lower back brackets 242 and 243 to be bent rearward. Furthermore, the left side panel 130 and the right side panel 140 of the cabinet 100 may be formed therein with locking ribs 131 having grooves 132 in which the side bending parts 241B, 242B, and 243B are inserted, respectively. The locking ribs 131 may protrude to lateral surfaces of the left side panel 130 and the right side panel 140 from rear surface of the left side panel 130 and the right side panel 140, respectively. The grooves 132 may be formed at bottom sides of the locking rib 131 so that top sides of the side bending parts 241B, 242B, and 243B are inserted into the grooves 132, respectively. The side bending parts 241B, 242B, and 243B may be inserted into the grooves 132 formed in the locking ribs 131 so that the frame body 210 does not oscillate in rightward and leftward when the frame body 210 is installed inside the cabinet 100.

Furthermore, an upper bending part 241C may be formed at a top end of the upper back bracket 241 to protrude rearward. The stiffness of the upper back bracket 241 is improved due to an upper bending part 241C, a side bending part 241B, and the second inclined part 241A.

Moreover, upper bending parts 242C and 243C may be formed at upper ends of the lower back brackets 242 and 243 to protrude rearward. Lower bending parts 242A and 243A may be formed at bottom ends of the lower back brackets 242 and 243 to protrude rearward. The stiffness of the lower back brackets 242 and 243 may be improved due to the lower bending parts 242C and 243C, the lower bending parts 242A and 243A, and the side bending parts 242B and 243B.

Figure 11:
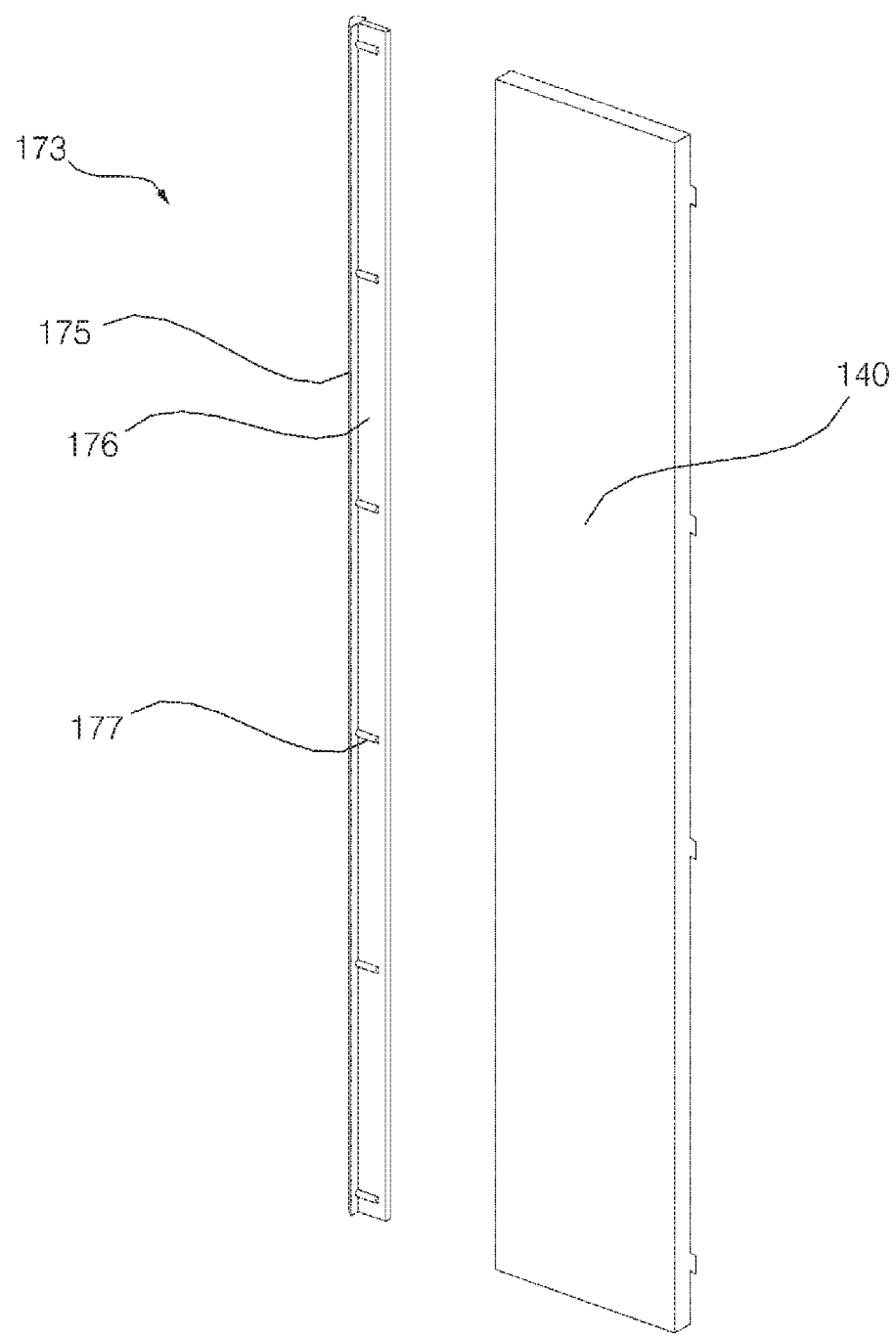
FIG. 11 is a left perspective view illustrating a right side panel and a decoration member shown in FIG. 4.

Hereinafter, an operation of coupling decoration members 171, 172, and 173 with the upper panel 110, the left side panel 130, and the right side panel 140 will be described with reference to FIG. 15 and FIG. 16. FIG. 11 is a left perspective view illustrating a right side panel and a decoration member shown in FIG. 4, and FIG. 12 is a right perspective view illustrating a right side panel and a decoration member shown in FIG. 4.

Figure 12:
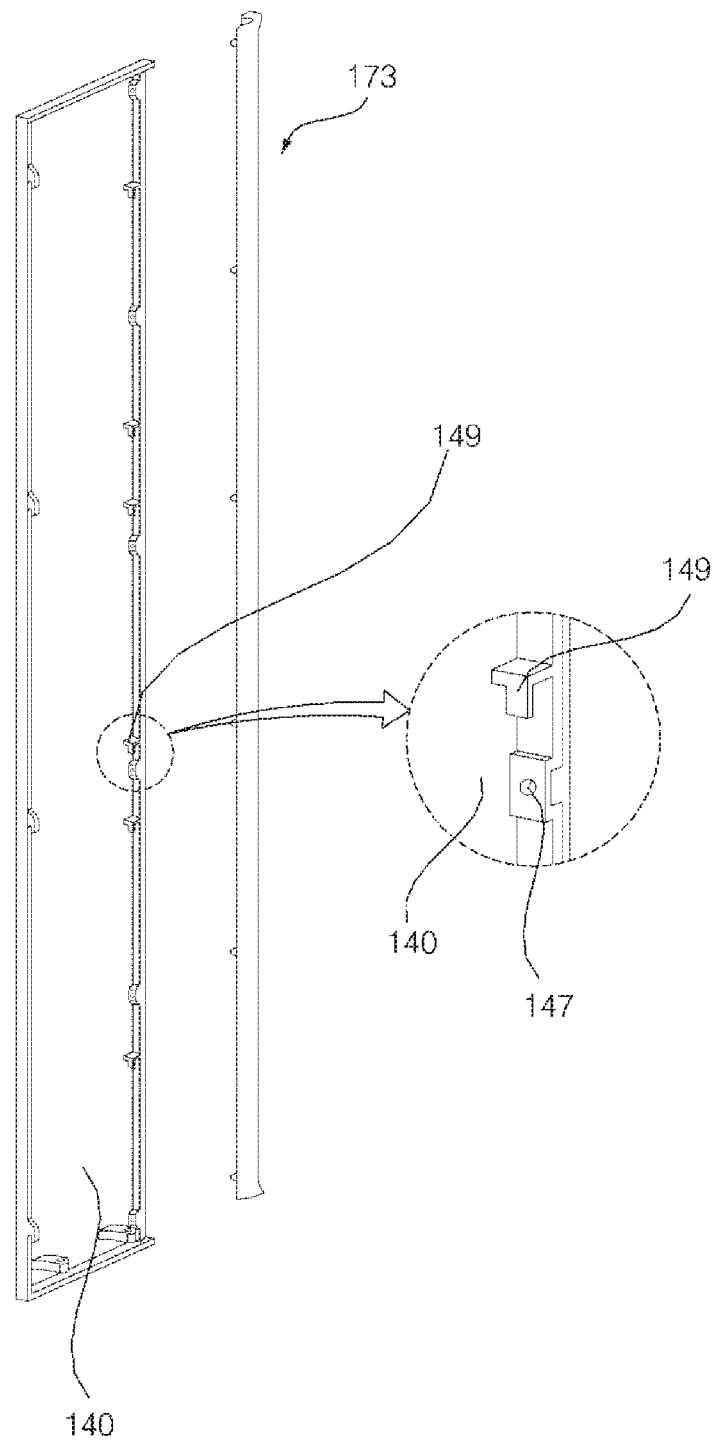
FIG. 12 is a right perspective view illustrating a right side panel and a decoration member shown in FIG. 4.

Referring to FIG. 11 and FIG. 12, the decoration members 171, 172, and 173 may include front surfaces 175 and lateral surfaces 176 protruding rearward of one side of the front surface 175. When the decoration members 171, 172, and 173 are installed at the upper panel 110, the left side panel 130, and the right side panel 140, the front surfaces 175 may be located at front ends of the left side panel 130 and the right side panel 140, respectively, and the lateral surfaces 176 are located at inner sides of the left side panel 130 and the right side panel 140.

Locking protrusions 177 may protrude rearward of front surfaces of the decoration members 171, 172, and 173. Although FIG. 15 and FIG. 16 illustrate that the locking protrusion 177 is formed at only the front surface of the third decoration member 173, the locking protrusions 177 as the locking protrusion may also be formed at the front surface of the first decoration member 171 and/or at the front surface of the second decoration member 172.

Further, first locking holes 147 in which the locking protrusion 177 is inserted and coupled, may be formed at a front end of the upper panel 110, a front end of the left side panel 130, and a front end of the right side panel 140. The locking protrusion 177 may be inserted and coupled in the first locking hole 147 so that the decoration members 171, 172, and 173 may be coupled with the upper panel 110, the left side panel 130, and the right side panel 140, respectively. Although FIG. 15 and FIG. 16 illustrate that the locking hole 147 is formed in only the right side panel 140, the first locking holes 147 may also be formed at the upper panel 110 and the left side panel 130, respectively.

Meanwhile, referring to FIG. 12, second module locking protrusions 149 may be formed in the left side panel 130 and the right side panel 140, respectively. The second module locking protrusions 149 may protrude inward of front ends of the left side panel 130 and the right side panel 140 and may be inserted into a module locking groove 635 formed at the first module locking protrusion 630 shown in FIG. 8 to fix the function modules 300, 400, 500, 600, and 700. Although FIG. 15 and FIG. 16 illustrate that the second module locking protrusion 149 is formed at only a front end of the right side panel 140, the second module locking protrusion 149 may also be formed at the front end of the left side panel 130.

As shown in FIG. 5 to FIG. 8, since the left side panel 130 and the right side panel 130 are coupled with the upper panel 110 and the lower panel 120 in a upward and downward sliding scheme when the left side panel 130 and the right side panel 140 slide upward and downward, the module locking groove 635 may be formed at a top side of the first module locking protrusion 630 so that the second module locking protrusion 149 is inserted into the module locking groove 635 to be locked with the first module locking protrusion 630.

Figure 13:
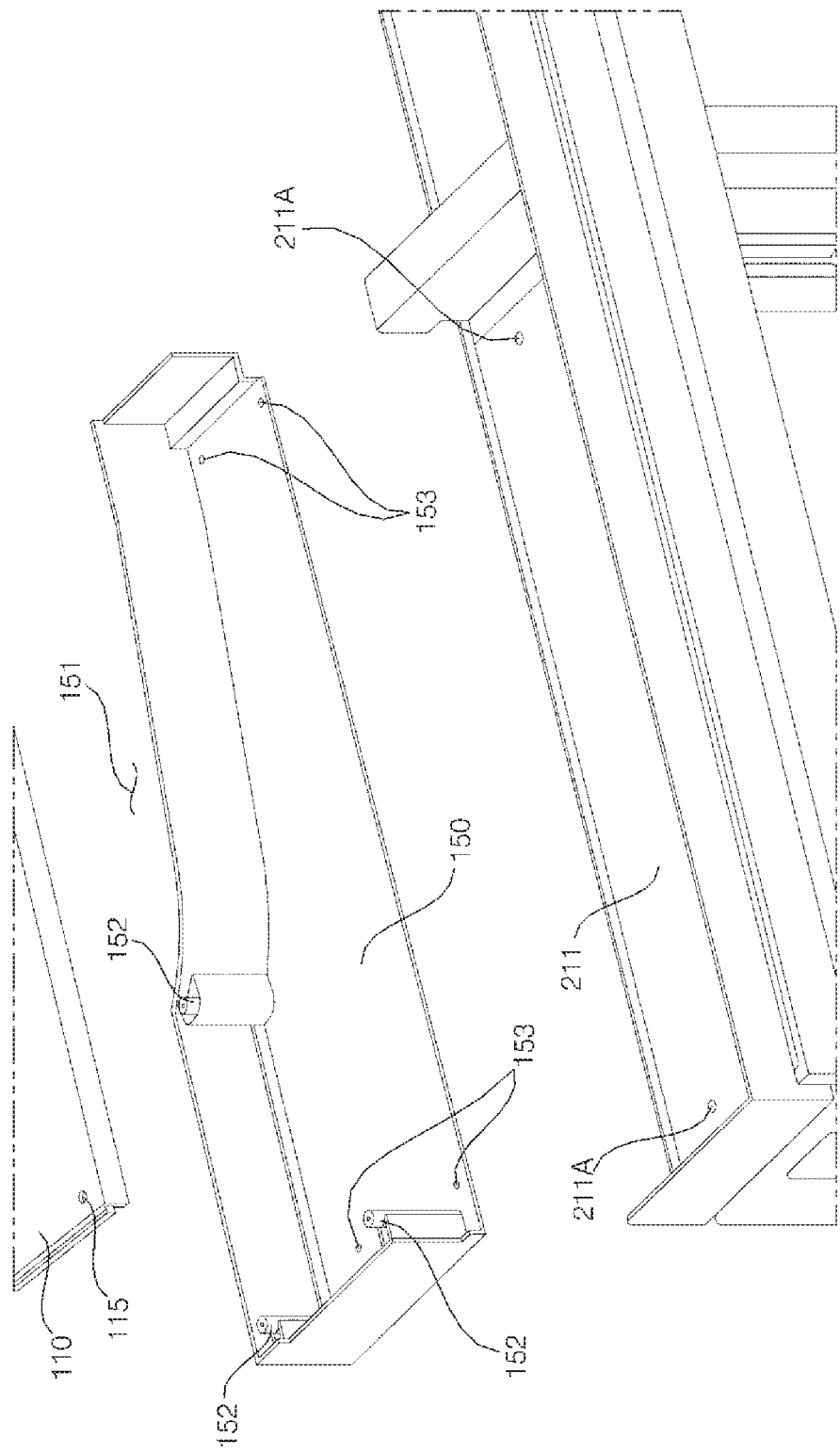
FIG. 13 is a view illustrating an upper panel, an upper cover, and an upper frame shown in FIG. 4.
Figure 14:
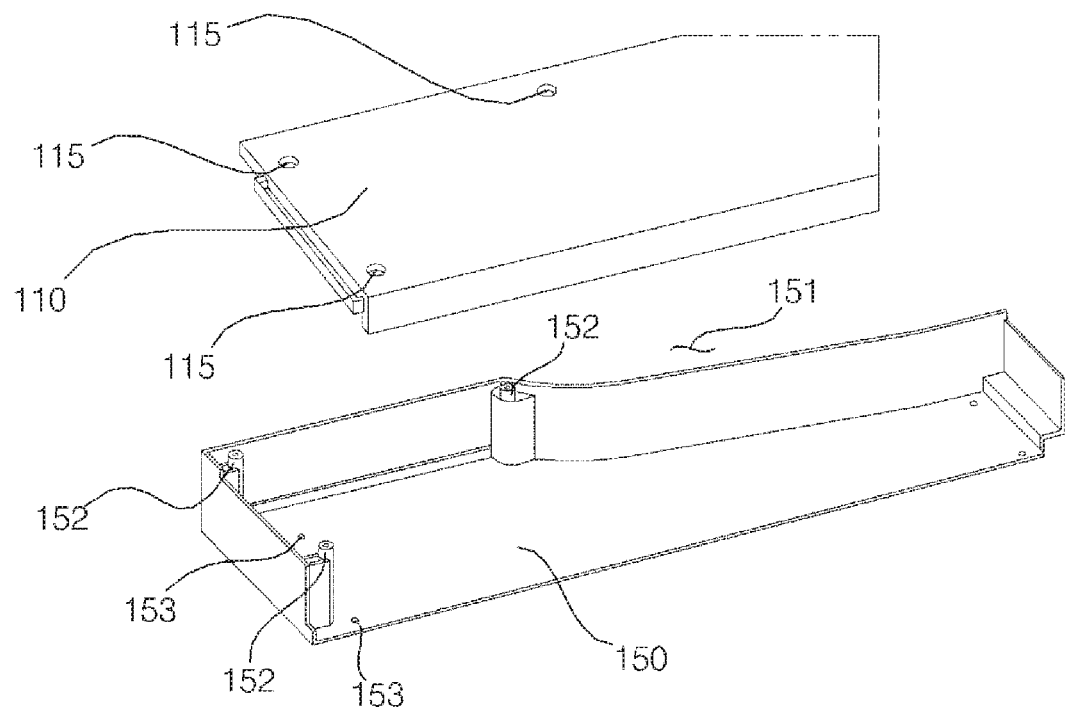
FIG. 14 is a view illustrating an upper panel and an upper cover shown in FIG. 4.

Hereinafter, an operation of coupling the upper cover 150 with the upper panel 110 and the upper frame 211 will be described with reference to FIG. 13 and FIG. 14. FIG. 13 is a view illustrating an upper panel, an upper cover, and an upper frame shown in FIG. 4, and FIG. 14 is a view illustrating an upper panel and an upper cover shown in FIG. 4. Referring to FIG. 13 and FIG. 14, the upper cover 150 may be formed therein with a first locking boss 152 locked with the upper panel 110 and a second locking hole 153 locked with the upper frame 211.

In one example, three first locking bosses 152 may be provided. Two first locking bosses 152 may be spaced apart from each other forward and rearward at an inner side of a lateral surface distant from a concave groove 151 of both lateral surfaces of the upper cover 150, and another first locking boss 152 may be formed a region close to the concave groove 151 in a front surface of the upper cover 150.

The upper panel 110 may be formed therein with a locking hole 115 locked with the first locking boss 152 through a screw or other fastener. On one implementation, the locking holes 115 may be formed at positions and in a quantity corresponding to those of the first locking bosses 152. A screw or other fastener may be inserted into the locking hole 115 in a top side of the upper panel 110 to lock the screw or other fastener with the locking boss 152 so that the upper cover 150 is locked with an upper panel 110 of the cabinet 100.

In one example, four second locking bosses 153 may be provided. Two second locking bosses 153 may be spaced apart from each other forward and rearward at a left region of a bottom surface of the upper cover 150, and another two two second locking bosses 153 may be spaced apart from each other forward and rearward at a right region of the bottom surface of the upper cover 150.

The upper frame 211 may include a locking hole 211A locked with the second locking boss 153 through a screw or other fastener. The locking holes 211A may be formed in locations and a quantity corresponding to those of the second locking holes 153. A screw or other fastener may be inserted into the locking hole 211A in a top side of the upper cover 150 to lock the screw with the locking hole 211A so that the upper cover 150 is locked with an upper frame 211 of the frame 200.

Hereinafter, an operation of coupling the control panel 160 with the lower frame 212 and the lower panel 120 will be described with reference to FIG. 15 and FIG. 16. FIG. 15 is an exploded perspective view illustrating a lower panel and a control panel shown in FIG. 4, and FIG. 16 is a combined perspective view illustrating a lower panel and a control panel shown in FIG. 4.

Figure 15:
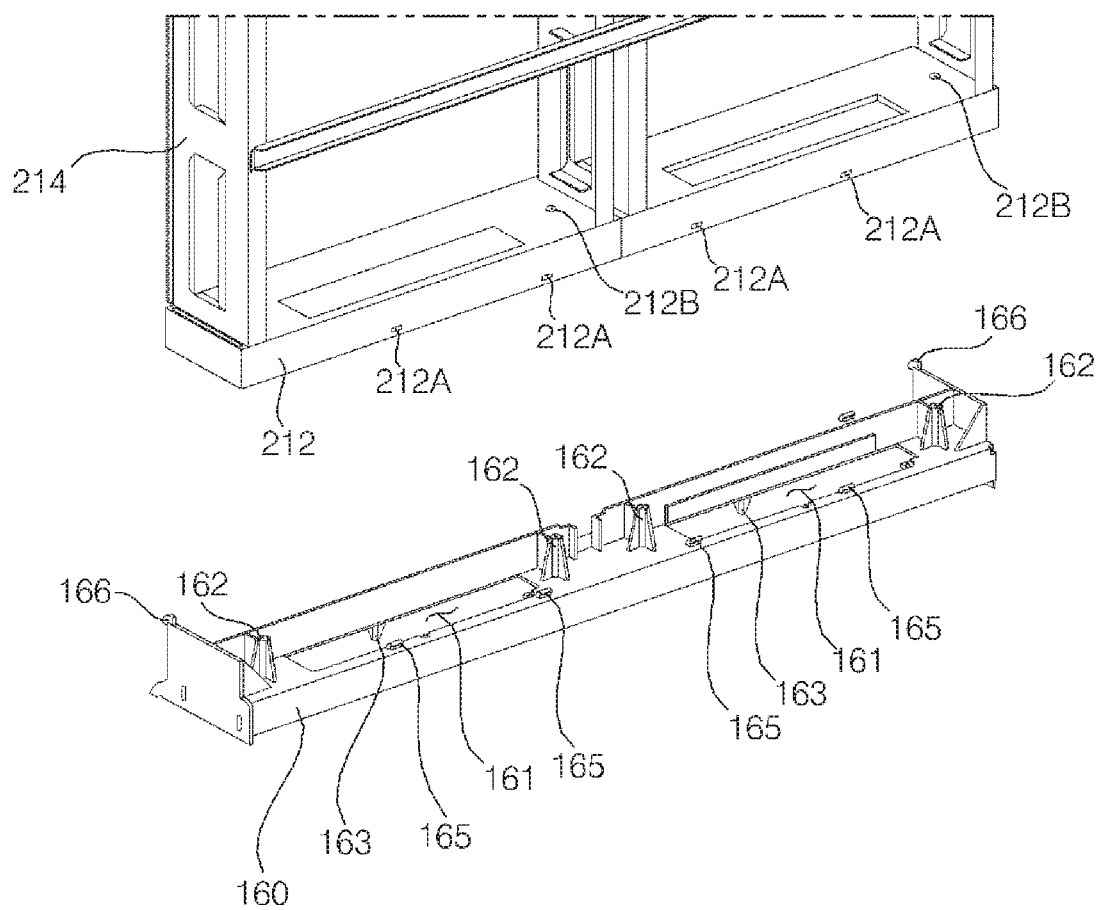
FIG. 15 is an exploded perspective view illustrating a lower panel and a control panel shown in FIG. 4.
Figure 16:
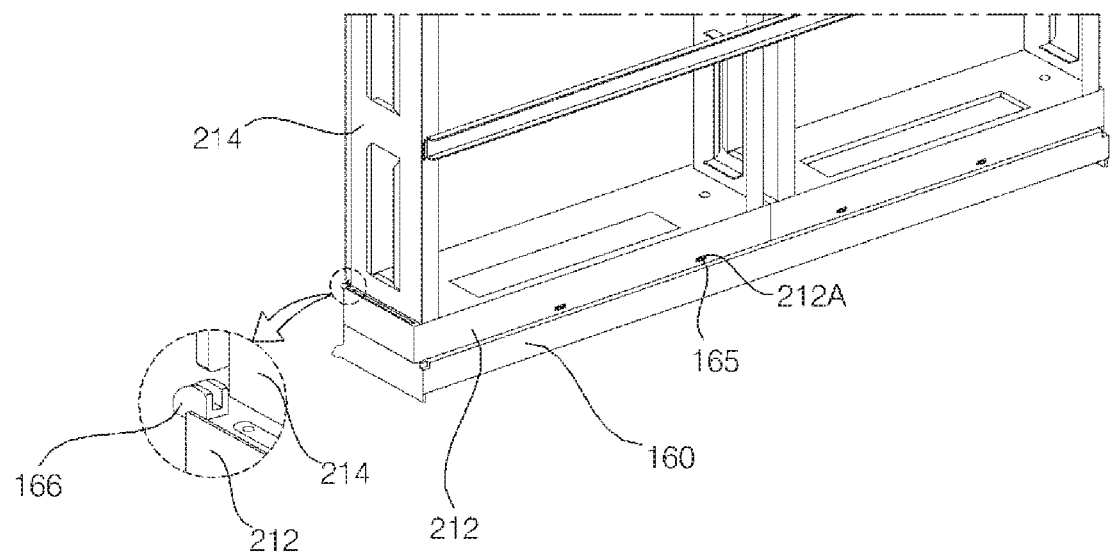
FIG. 16 is a combined perspective view illustrating a lower panel and a control panel shown in FIG. 4.

Referring to FIG. 8, FIG. 15, and FIG. 16, a hook hole 212A may be formed at a rear surface of the lower frame 212. A plurality of hook holes 212A may be spaced apart from each other rightward and leftward. In certain embodiments, two hook holes 212A may be formed in one of frame bodies 210 and 220.

Further, the control panel 160 may be formed therein with a first hook protrusion 165 inserted and locked in the hook hole 212A and a second hook protrusion 166 locked with a top end of the lower frame 212. The hook protrusions 165 may be formed at positions and in a quantity corresponding to those of the hook holes 212A. The hook protrusion 165 may protrude downward of a rear side of a top surface of the control panel 160. The second hook protrusion 166 may protrude rearward of a front end of both sides of the control panel 160. The control panel 160 may be moved rearward from a forward direction of the lower frame 212 to insert the first hook protrusion 165 into the hook hole 212A, and to lock the second hook protrusion 166 with a top end of the lower frame, so that the control panel 160 is optionally locked with a lower frame 212 of the frame 200.

The control panel 160 is further formed therein with a second locking boss 162 locked with the lower frame 212 of the frame 200 and a third locking boss 163 locked with a lower panel 120 of the cabinet 100. The second locking boss 162 protrudes upward from a top surface of the control panel 160, and the third locking boss 163 protrudes downward from a bottom surface of the control panel 160.

A plurality of second locking bosses 162 may be spaced apart from each other rightward and leftward. In the present embodiment, two second locking bosses 162 may be formed in one of frame bodies 210 and 220. Further, the lower frame 211 may be formed therein with a locking hole 211A that is locked with the second locking boss 153 through a screw or other fastener. The locking holes 212B may be formed in quantities and at positions corresponding to the second locking bosses 162.

After a control panel 160 is optionally locked with the lower frame 212 using the first hook protrusion 165 and the second hook protrusion 166, a screw or other fastener may be inserted into the locking hole 212B at a top side of the lower frame 212 and then the screw or other fastener may be locked with the second locking boss 162, so that the control panel 160 may be locked with a lower frame 212 of the frame 200. In addition, a locking rib 124 formed on a top surface of the lower panel 120 may be locked with a third locking boss 163 formed at a top surface of the control panel 160 by inserting the screw or other fastener into a lower surface of the lower panel 120 of the cabinet 100 so that the control panel 160 may be locked with a lower panel 120 of the cabinet 100.

In the bathroom management apparatus of an embodiment of the present disclosure, the cabinet 100, the upper panel 150, and the control panel 160 may be coupled with the frame 200 to be firmly supported. Furthermore, since the left side panel 130 and the right side panel 140 are slidably coupled with the upper panel 110 and the lower panel 120 upward and downward, when one or more of the function modules 300, 400, 500, 600, 700, 800, and 810 installed in the frame 200 fail, the left side panel 130 and the right side panel 140 may be slid upward to be separated while maintaining the bathroom management apparatus installed on a bathroom wall, and the faulty function module(s) 300, 400, 500, 600, 700, 800, and 810 may be easily separated from the frame 200 to be repaired.

While the present disclosure has been shown and described in connection with the embodiments, it will be apparent to those skilled in the art that modifications and variations can be made without departing from the spirit and scope of the disclosure as defined by the appended claims.

A first aspect of the present disclosure provides a firm bath management apparatus. A second aspect of the present disclosure provides a bath management apparatus capable of easily repairing failure of a function module.

According to the aspects of the present disclosure, a bathroom management apparatus includes: a cabinet of which a front surface is open; a frame installed at an inner side of the cabinet to reinforce stiffness of the cabinet and of which an upper side and a lower side are spaced apart from the cabinet; an upper cover provided between the cabinet and the upper side of the frame to be coupled with the cabinet and the frame and configured to cover a space between the cabinet and the upper side of the frame; and a control panel provided between the cabinet and the lower side of the frame to be coupled with the cabinet and the frame and installed therein with a user interface.

The cabinet may include an upper panel forming an upper side, a lower panel forming a lower side, a left side panel forming a left side, and a right side panel forming a right side, first end ribs having first end grooves at top sides of the first end ribs are formed at both ends of the upper panel, respectively, second end ribs inserted into the first end grooves are formed at an inner side of the left side panel and an inner side of the right side panel, respectively, third end ribs having second end grooves at top sides of the third end ribs are formed at top sides of both ends of the lower panel, respectively, and fourth end ribs inserted into the second end grooves are formed at the inner side of the left side panel and the inner side of the right side panel, respectively.

According to the aspects of the present disclosure, the cabinet, the upper panel, and the control panel may be coupled with the frame to be firmly supported. According to the aspects of the present disclosure, since the left side panel and the right side panel are slidably coupled with the upper panel and the lower panel upward and downward, when various function modules installed in the frame fail, the left side panel and the right side panel are slid upward to be separated while maintaining the bathroom management apparatus installed on a bathroom wall, and the function module may be easily separated from the frame to be repaired.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present disclosure.

Spatially relative terms, such as "lower", "upper" and the like, may be used herein for ease of description to describe the relationship of one element or feature to another element (s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the disclosure. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A bathroom management apparatus comprising:
    a cabinet having a front side that is open;
    a frame installed in the cabinet to reinforce a stiffness of the cabinet and having an upper side and a lower side that are spaced apart from the cabinet;
    an upper cover provided between the cabinet and the upper side of the frame to be coupled to the cabinet and the frame, and configured to cover a space between the cabinet and the upper side of the frame; and
    a control panel having a user interface and provided between the cabinet and the lower side of the frame to be coupled to the cabinet and the frame,
    wherein:
        the cabinet includes an upper panel forming an upper side of the cabinet, a lower panel forming a lower side of the cabinet, a left side panel forming a left side of the cabinet, and a right side panel forming a right side of the cabinet,
        the frame includes a frame body installed inside of the cabinet, and a back bracket coupled to a rear of the frame body to reinforce stiffness of the frame body,
        the back bracket includes side bending extensions that are bent rearward of ends of the back bracket, and
        locking ribs having grooves at bottom sides of the ribs and in which the side bending extensions are inserted are formed at rear sides of the left and right side panels of the cabinet.

2. The bathroom management apparatus of claim 1, wherein
    first end ribs having first end grooves at top sides of the first end ribs are formed at both ends of the upper panel,
    second end ribs inserted into the first end grooves are formed at an inner side of the left side panel and an inner side of the right side panel, respectively,
    third end ribs having second end grooves at top sides of the third end ribs are formed at top sides of both ends of the lower panel, respectively, and
    fourth end ribs inserted into the second end grooves are formed at the inner side of the left side panel and the inner side of the right side panel, respectively.

3. The bathroom management apparatus of claim 1, wherein
    the bathroom management apparatus further comprises decoration panels coupled to a front end of the upper panel, a front end of the left side panel, and a front end of the right side panel,
    a locking protrusion is formed at the decoration panels, and
    first locking holes are formed at the front end of the upper panel, the front end of the left side panel, and the front end of the right side panel so that the locking protrusions are inserted and locked in the first locking holes, respectively.

4. The bathroom management apparatus of claim 1, wherein
    the bathroom management apparatus further comprises:
        a door configured to selectively cover an open front surface of the cabinet; and
        a hinge provided at a rear top side of the door to be coupled to the upper frame, and
    a concave groove to receive the hinge when the door is closed is formed at a front surface of the upper cover.

5. The bathroom management apparatus of claim 1, wherein
the frame includes an upper frame forming an upper side if the frame, a lower frame forming a lower side of the frame, a left side frame forming a left side of the frame, and a right side frame forming a right side of the frame, and
the upper cover includes a first locking boss that couples to the upper panel, and a second locking hole that couples to the upper frame.

6. The bathroom management apparatus of claim 1, wherein the frame includes an upper frame forming an upper side of the frame, a lower frame forming a lower side of the frame, a left side frame forming a left side of the frame, and a right side frame forming a right side of the frame,
a hook hole is formed at a rear surface of the lower frame, and
the control panel includes a first hook protrusion configured to be inserted into the hook hole and a second hook protrusion configured to be coupled to a top end of the lower frame.

7. The bathroom management apparatus of claim 6, wherein the control panel is further includes a second locking boss configured to be coupled to the lower frame and a third locking boss configured to be coupled to the lower panel.

8. The bathroom management apparatus of claim 1, wherein a plurality of frames are provided, and
the bathroom management apparatus further comprises one or more center covers that cover adjacent side frames of the plurality of frames.

9. The bathroom management apparatus of claim 1, wherein
the frame includes an upper frame forming an upper side of the frame, a lower frame forming a lower side of the frame, a left side frame forming a left side of the frame, and a right side frame forming a right side of the frame,
the upper frame and the lower frame include cut lines, respectively,
second openings are formed at the upper frame and the lower frame when an inner region divided by the cut line is separated,
a third opening is formed below the second opening in the control panel,
a fourth opening is formed below of the third opening portion of the lower panel of the cabinet.

10. The bathroom management apparatus of claim 9, further comprising a blower louver coupled to the lower panel corresponding to the fourth opening and including a discharge grill.

11. The bathroom management apparatus of claim 9, wherein further comprising a lower cover coupled to the lower panel at a position corresponding to the fourth opening to cover the fourth opening.

12. The bathroom management apparatus of claim 1, wherein the frame is included in a plurality of frames installed in the interior of the cabinet, and the bathroom management apparatus further includes a plurality of doors positioned over, respectively the plurality of frames.

13. The bathroom management apparatus of claim 12, further comprising:
a plurality of mirrors positioned over, respectively, front surfaces of the plurality of doors.

14. The bathroom management apparatus of claim 13, further comprising:
a plurality of hinges coupled to the door and the upper frame, and
concave grooves formed at a front surface of the upper cover and configured to receive the hinges when the doors are closed.

15. The bathroom management apparatus of claim 1, further comprising one or more function modules received in the frame.

16. The bathroom management apparatus of claim 15, wherein the one or more function modules include a towel care module to receive and dry a towel, a sterilizing module to sterilize an object, a secret box module to provide an enclosure to receive an object, a refrigerating module to receive and cool makeup, a charging module to receive and charge an electronic device, or a blower out module to output an air flow to one of a user or a bathroom surface.

17. The bathroom management apparatus of claim 15, wherein the frame includes first openings to receive wires of the one or more function modules.

18. The bathroom management apparatus of claim 1, wherein
a first air outlet is formed in a space between the lower side the frame and a top side of the control panel,
a second air outlet is formed on a lower panel of the cabinet, and
a module received in the frame outputs an air flow through the first and second air outlets.

19. The bathroom management apparatus of claim 18, wherein the second air outlet includes a blower louver coupled to the lower panel and including a discharge grill.

20. A bathroom management apparatus comprising:
a cabinet having a front side that is open;
a frame installed in the cabinet to reinforce a stiffness of the cabinet and having an upper side and a lower side that are spaced apart from the cabinet;
an upper cover provided between the cabinet and the upper side of the frame to be coupled to the cabinet and the frame, and configured to cover a space between the cabinet and the upper side of the frame; and
a control panel having a user interface and provided between the cabinet and the lower side of the frame to be coupled to the cabinet and the frame,
wherein:
the cabinet includes an upper panel forming an upper side of the cabinet, a lower panel forming a lower side of the cabinet, a left side panel forming a left side of the cabinet, and a right side panel forming a right side of the cabinet,
first end ribs having first end grooves at top sides of the first end ribs are formed at both ends of the upper panel,
second end ribs inserted into the first end grooves are formed at an inner side of the left side panel and an inner side of the right side panel, respectively,
third end ribs having second end grooves at top sides of the third end ribs are formed at top sides of both ends of the lower panel, respectively, and
fourth end ribs inserted into the second end grooves are formed at the inner side of the left side panel and the inner side of the right side panel, respectively.

* * * * *